United States Patent
Onishi et al.

(10) Patent No.: US 9,481,832 B2
(45) Date of Patent: Nov. 1, 2016

(54) FLAME RETARDANT COMPOSITION FOR FLAMMABLE PLASTIC MATERIALS COMPRISING 2,4,6-TRIS(2,4,6-TRIBROMO-PHENOXY)-1,3,5-TRIAZINE AND PROCESS FOR PRODUCING THE SAME

(71) Applicants: DAI-ICHI KOGYO SEIYAKU CO., LTD., Kyoto-shi, Kyoto-fu (JP); BROMINE COMPOUNDS, LTD., Beer Sheva (IL)

(72) Inventors: Hideaki Onishi, Kyoto (JP); Michael Peled, Beer Sheva (IL)

(73) Assignees: DAI-ICHI KOGYO SEIYAKU CO., LD., Kyoto-Shi (JP); BROMINE COMPOUNDS, LTD., Beer Sheva (IL)

( * ) Notice: Subject to any disclaimer, the term of this patent is extended or adjusted under 35 U.S.C. 154(b) by 0 days.

(21) Appl. No.: 14/733,444

(22) Filed: Jun. 8, 2015

(65) Prior Publication Data

US 2015/0267120 A1    Sep. 24, 2015

Related U.S. Application Data

(63) Continuation of application No. 13/265,628, filed as application No. PCT/JP2009/001982 on May 1, 2009.

(51) Int. Cl.
| | |
|---|---|
| *C09K 21/10* | (2006.01) |
| *C07D 251/30* | (2006.01) |
| *C08K 3/00* | (2006.01) |
| *C08K 5/00* | (2006.01) |
| *C08K 5/3492* | (2006.01) |
| *C08K 13/02* | (2006.01) |

(52) U.S. Cl.
CPC .............. *C09K 21/10* (2013.01); *C07D 251/30* (2013.01); *C08K 3/0058* (2013.01); *C08K 5/0066* (2013.01); *C08K 5/3492* (2013.01); *C08K 13/02* (2013.01)

(58) Field of Classification Search
None
See application file for complete search history.

(56) References Cited

U.S. PATENT DOCUMENTS

2007/0228344 A1    10/2007    Bar-Yaakov et al.

FOREIGN PATENT DOCUMENTS

| CN | 1830969 | | 9/2006 |
|---|---|---|---|
| EP | 0735084 | A1 | 10/1996 |
| JP | 2003128859 | A | 5/2003 |
| KR | 2005074062 | A | 7/2005 |
| WO | 2008071214 | A1 | 6/2008 |

OTHER PUBLICATIONS

Translation of Ding, CN 1830969, dated Sep. 2006.
Abstract of JP 2003-128859, May 8, 2003, Database WPI Week 200427, Thomson Scientific, London, GB, XP-002545994, pp. 1-3, cited in International Search Report, dated Sep. 30, 2009, issued in corresponding PCT/JP2009/001982.
Abstract of Ning, S, et al., "Synthesis of tris(2,4,6-tribromophenoxy)-1,3,5-triazine," Mar. 13, 2008, Chemical Abstracts Service, Columbus, Ohio, US, XP-002546094, 1 page, cited in International Search Report, dated Sep. 30, 2009, issued in corresponding PCT/JP2009/001982.
Abstract of JP 08 012865 A, Jan. 16, 1996, Database WPI Week 199612, Thomson Scientific, London, GB, XP-002546074, pp. 1-2, cited in International Search Report, dated Sep. 30, 2009, issued in corresponding PCT/JP2009/001982).
Chen, J., et al., "Effect of a Type of Triazine on the Properties and Morphologies of Poly(butylene terephthalate) Composites." Journal of Applied Polymer Science Wiley USA, (2006), vol. 102, No. 2, pp. 1291-1296, cited in International Search Report, dated Sep. 30, 2009, issued in corresponding PCT/JP2009/001982).
International Search Report, dated Sep. 30, 2009, issued in corresponding PCT/JP2009/001982.

*Primary Examiner* — Tanisha Diggs
(74) *Attorney, Agent, or Firm* — Miller, White, Zelano, Branigan, P.C.

(57) ABSTRACT

A flame retardant composition for flammable plastic materials and a method for producing the same are disclosed. The flame retardant composition comprises 2,4,6-tris(2,4,6-tribromophenoxy)-1,3,5-triazine that contains 1 to 1000 ppm of a metal species of a water-insoluble polyvalent metal compound selected from the group consisting of oxide, hydroxide, carbonate, phosphate, sulfate and silicate present in the particles of 2,4,6-tris(2,4,6-tribromophenoxy)-1,3,5-triazine. The flame retardant composition is produced by reacting an alkali metal salt of 2,4,6-tribromophenol and cyanuric chloride in the presence of said water-insoluble polyvalent metal compound.

16 Claims, No Drawings

FLAME RETARDANT COMPOSITION FOR FLAMMABLE PLASTIC MATERIALS COMPRISING 2,4,6-TRIS(2,4,6-TRIBROMO-PHENOXY)-1,3,5-TRIAZINE AND PROCESS FOR PRODUCING THE SAME

TECHNICAL FIELD

The present invention relates to a flame retardant composition for flammable plastic materials comprising 2,4,6-tris(2,4,6-tribromophenoxy)-1,3,5-triazine. It also relates to a process for producing said flame retardant composition.

BACKGROUND ART 2,4,6-Tris(2,4,6-tribromophenoxy)-1,3,5-triazine has been used as a flame retardant for plastic products. This compound may be synthesized by reacting cyanuric chloride with an alkali metal phenolate, typically sodium phenolate. During the reaction, an alkali metal halide, typically sodium chloride is formed as a by-product and thus the resulting product may be contaminated with a halide ion source. The product contaminated with the halide-ion source may result in various shortcomings when used as a flame retardant for flammable plastic materials. When thermoplastic materials are rendered flame retarded it is conventional to blend the thermoplastic material and the flame retardant in molten state and the molten blend is molded into shaped articles. The halide ions from their source contained in the flame retardant may promote corrosion of metallic parts of extruders or other mixing apparatus as well as molds and other metallic parts of shaping machines. The halide ions per se and rust pieces resulting from the corrosion of mixing or shaping machine parts may adversely affect the performance of shaped articles including heat resistance, electrical properties and tracking resistance in particular. Flame retardants are blended with thermosetting plastic materials for rendering them flame retarded. In this case, a dispersion or solution of solid flame retardant powder is added, for instance, to a resin varnish. Then prepregs are prepared from the varnish for fabricating a metal clad laminate for the production of a printed circuit board. If the flame retardant contains a halide ion source at unacceptable level, the electrical properties of the board is greatly compromised.

2,4,6-Tris(2,4,6-tribromophenoxy)-1,3,5-triazine (hereinafter simply called "brominated phenoxytriazine") was first described in French Patent No. 1,566,675 wherein the compound is synthesized by adding a suspension of cyanuric chloride in acetone to a solution of sodium 2,4,6-tribromophenolate in benzene/acetone mixture.

U.S. Pat. No. 3,843,650 discloses the synthesis of brominated phenoxytriazine by the addition of cyanuric chloride to an ethanolic solution of sodium tribomophenolate. U.S. Pat. No. 5,965,731 discloses the synthesis of brominated phenoxytriazine by successively adding an aqueous solution of sodium hydroxide and a solution of cyanuric chloride in acetone to a solution of tribormophenol in acetone.

U.S. Pat. No. 4,039,538 discloses a reaction of an alkali metal tribromophenolate dissolved in an alkylene glycol monoalkyl ether such as methyl- or ethylcellosolve with cyanuric chloride.

JP 7/25859A, JP 7/25860A and JP 7/25861A disclose a reaction between a concentrated aqueous tribromophenolate solution/methylene chloride mixture and a solution or suspension of cyanuric chloride in methylene chloride in the presence of a tertiary amine and/or phase transfer catalyst.

Whichever process is employed, the concentration of alkali metal halide such as NaCl or KCl in the reaction system increases as the reaction proceeds. At the same time, brominated phenoxytriazine formed will crystallize out because its solubility in water and organic solvents is very low. Therefore, it is inevitable to entrain the halide salt by brominated phenoxytriazine when crystallizing from the reaction mixture. In order to minimize the entrainment of the halide salt, it would be effective to maintain the concentration of the halide salt in the reaction system as low as possible by decreasing the amounts of charged alkali metal phenolate and cyanuric chloride per unit volume of the reaction medium. This approach naturally decreases the amount of the target product to be recovered as crystals and is, therefore, hardly applicable to an industrial scale production due to low productivity.

Once contained in the crystals, it is difficult to remove the halide salt from brominated phenoxytriazine by washing with a solvent of the halide salt such as water, ethanol or acetone. Accordingly, one of other conceivable approaches to reduce the halide salt content would be dissolving the crystals containing the halide salt in a large volume of an organic solvent in which the crystals are soluble and recrystalling the product from the solution, or reverse extracting the halide salt from the above solution and then evaporating the organic solvent. It is also conceivable to repeat the washing of finely divided crystals containing the halide salt with water or ethanol. However, all of these approaches are hardly applicable to an industrial scale production due to low productivity.

Accordingly, a need exists for a flame retardant composition comprising 2,4,6-tris(2,4,6-tribromophenoxy)-1,3,5-triazine which has a minimum content of halide salts and other deteriorative impurities. Also, a need exists for a process for producing said flame retardant composition.

SUMMARY OF INVENTION

According to the present invention, there is provided a flame retardant composition for flammable plastic materials comprising particulate 2,4,6-tris(tribrophenoxy)-1,3,5-triazine containing 1 to 1000 ppm of a metal species of a water-insoluble polyvalent metal compound selected from the group consisting of oxide, hydroxide, carbonate, phosphate, sulfate and silicate, said water-insoluble polyvalent metal compound being present in said particulate 2,4,6-tris(2,4,6-tribromophenoxy)-1,3,5-triazine in a physically indiscrete form.

The present invention also provides a process for producing said flame retardant composition comprising reacting an alkali metal tribromophenolate and cyanuric chloride in the presence of 0.01 to 10% by weight of cyanuric chloride of finely divided particles of a water-insoluble polyvalent metal compound selected from the group consisting of oxide, hydroxide, carbonate, phosphate, sulfate and silicate.

Although the invention is not bound to any particular theory, it is postulated that the finely divided water-insoluble polyvalent metal compound present in the reaction system serves as a nucleus for growing crystals, and promote, as the reaction proceeds, crystallization of brominated tribromophenoxytriazine without entraining the halide salt in the crystals. Instead, the product produced according to present invention contains more than 1 ppm of a metal species corresponding to the polyvalent metal compound employed. The presence thereof, however, does not have any adverse effect on the flame retarded plastic articles and shaping machines therefore.

In another aspect, the present invention provides said flame retardant composition having reduced content of halide ion sources produced by the method of the present invention wherein the product contains 1 to 1000 ppm of at least one metal species corresponding to said polyvalent metal compound.

DESCRIPTION OF EMBODIMENTS

Except the reaction is carried out in the presence of said water-insoluble polyvalent metal compound, the process of the present invention may be otherwise identical to those known in the art including the processes disclosed in the patents cited above.

The process of the present invention may be carried out by adding said insoluble multivalent metal compound to any of reaction systems according to the above known processes. The insoluble metal salt which may be employed in the present invention includes oxide, hydroxides, carbonates, phosphates, sulfates or silicates of a polyvalent metal such as magnesium, calcium, barium, aluminum, silicon, titanium, zirconium or antimony. Examples thereof include magnesium hydroxide, magnesium carbonate, magnesium phosphate, magnesium sulfate, magnesium silicate, calcium hydroxide, calcium carbonate, calcium phosphate, calcium sulfate, calcium silicate, barium carbonate, barium phosphate, barium sulfate, aluminum oxide, aluminum carbonate, aluminum phosphate, aluminum silicate, silicon oxide (silica), titanium dioxide, zirconium dioxide and antimony trioxide. Naturally occurring or synthetic minerals comprising a polyvalent metal silicate complex such as talc, bentonite, kaolin or zeolite may also be used. Calcium carbonate, silica, barium sulfate, talc, aluminum polyphosphate, zirconium dioxide, titanium dioxide, antimony trioxide and calcium silicate are particularly preferred because they serve to prevent coloring and decomposition of a plastic material when blending with the flame retardant composition at an elevated temperature.

The term "water-insoluble polyvalent metal compound" as used herein refers to the compound having a solubility in water of less than 1 g/L, preferably less than 0.5 g/L at 25° C. As stated before, the finely divided insoluble polyvalent compound appear to serve as a nucleus of crystallization. For this reason, it is advantageous for the finely divided particles to have a large number of discrete particles per unit weight to minimize the amount of the metal compound to be added. Preferably, the particles have a mean diameter of less than 10 microns, more preferably less than 5 microns. Of particularly preferably particles are fumed silica having a mean diameter of nanometer order.

The amount of addition of the finely divided polyvalent metal compound generally ranges from 0.01 to 10% by weight of cyanuric chloride but it may vary depending upon the number of particles per unit weight, namely the mean diameter thereof. The smaller in the mean diameter, the fewer amount of addition.

The finely divided particles of the polyvalent metal compound are needed to exist in the reaction system before the crystallization of the reaction product takes place. Typically the finely divided particles are initially added to either one of the reactants, for example, to a solution of phenolate. The cyanuric chloride reactant may subsequently be added to the phenolate solution. Alternatively, the finely divided particles may be added to a solution of phenolate together with the cyanuric chloride reactant. Instead of pre-formed finely divided particles, it is possible to form the finely divided particles in situ in the reaction system as a slurry. For example, calcium carbonate may be formed in the reaction system by the reaction of calcium chloride and sodium carbonate. Similarly calcium phosphate may be formed by the reaction of calcium chloride and sodium phosphate.

The reaction may be carried out at a temperature from room temperature to the boiling point of the reaction medium. However, it is preferable to continue the reaction to completion at reflux temperature of the reaction mixture after all reactants have been added to the reaction vessel. After the reaction, the precipitated reaction product is filtered off, washed and dried. The filtration may be carried out using a conventional filter device or a centrifuge and washing of the resulting filter cake may be carried out thereon using water or a mixture of water and an organic solvent in which the alkali metal halide is soluble. The organic solvent is preferably a water-miscible solvent including methanol, ethanol, isopropanol, ethylene glycol, glycerine, acetone, DMF, THF, dioxane and the like. The washing efficiency is enhanced by the use of a water-miscible organic solvent due to enhanced affinity between the brominated phenoxytriazine and the solvent. However, it is preferable to use water alone in the final washing step to eliminate emission of VOC to the atmosphere upon drying the end product.

According to the present invention, the amount of halide ion source contaminants is reduced to less than 500 ppm calculated as NaCl. This amount may be reduced further to less than 250 ppm by suitably selecting particular kind of insoluble polyvalent metal compounds and their particle size. Instead, the product contains the finely divided polyvalent metal compound from 1 ppm to 1000 ppm calculated as the metal species corresponding to said water-insoluble metal compound. Such a small amount of the water-insoluble metal compound has no or little effect on the performance of the reaction product and shaped plastic articles containing the same. Namely, the flame retardant composition neither deteriorates the heat stability of shaped plastic articles nor promotes corrosion of mixing and shaping machines.

The amount of halide ions entrained into the reaction product may be determined by the potentiometric titration with $AgNO_3$ as outlined below, while the amount of metal species of the water-insoluble metal compound may be determined by the atomic absorption spectrometry or the inductively coupled plasma method.

In addition to the halide salt produced as a by-product, other electrolytes such as unreacted alkali metal phenolate may be present in the reaction system. They may also be entrained into the resulting brominated phenoxytriazine crystals. These electrolyte impurities also have an adverse effect on the electrical properties of the plastic articles containing the contaminated reaction product. These other electrolytic impurities are incapable of detecting by the potentiometric titration with $AgNO_3$ but capable of detecting quantitatively by leaching the crystals with water and measuring the electroconductivity of water containing the electrolytic impurities. According to the present invention, it is possible to reduce the halide ion level as determined by the potentiometric titration with $AgNO_3$ to less than 500 ppm calculated as NaCl and at the same time, to decrease the total level of electrolytes including the halide salt represented by the electroconductivity of leaching water to an acceptable level of less than $50 \times 10^{-6}$ S/cm.

Contrary to the present invention, the corresponding reaction products produced by similar processes in the absence of the finely divided water-insoluble metal compound showed to contain at least 1000 ppm of the halide ion sources and an electroconductivity level of leaching water higher than 150×10⁻⁶ S/cm. These halide ion levels and the electroconductivity levels could not be decreased to an acceptable level by washing the crystals as produced or pulverized crystals with methanol.

EXAMPLES

The invention will now be illustrated by the following examples. All parts and percents therein are by weight unless otherwise indicated.

Part I. Production of Brominated Phenoxytriazine

Materials
(1) Cyanuric chloride: industrial grade F available from Deggussa, 99.7% purity, metal content<10 ppm.
(2) Calcium carbonate: Nanox #30, available from Maruo Calcium Co., Ltd., mean diameter about 1 micron.
(3) Titanium dioxide; PF711 available from Ishihara Sangyo Kaisha, mean diameter about 0.25 microns.
(4) Fumed silica; Aerosil 200 available from Japan Aerosil, mean diameter 12 nm.
(5) Precipitated barium sulfate; available from Toshin Kasei Co., Ltd., mean diameter 0.5 microns.
(6) Talc (magnesium silicate); Microace P-3 available from Nippon Talc Co. Ltd., mean diameter 5 microns.
(7) Aluminum polyphosphate ($AlH_2P_3O_{10}$-$2H_2O$); K-White #85 available from Tayca Corporation, mean diameter 3.7 microns.
(8) Zirconium dioxide; EP grade available from Daiichi Rare Elements Chemical Industry Co., Ltd., mean diameter 2.2 microns.
(9) Antimony trioxide; AN-800(T) available from Dai-ichi Kogyo Seiyaku Co., Ltd., means diameter 1.1 microns.

Test Method
(1) Quantitative Analysis of Metals in Samples

The inductively coupled plasma method was used by dissolving the sample in DMF. First, a standard curve was generated using specimens having known contents of the metal. Then the metal content of a test sample having unknown metal content was determined by the intrapolation method. An IPC analyzer CIROS-120 available Rigaku was used.

(2) Determination of NaCl Content 5.0 g of the sample was precisely weighed in a 100 ml beaker and dissolved in 50 ml of dioxane completely. To the solution was added 5 ml of deionized water with stirring. Then the halide ion concentration of the resulting solution was determined by the potentiometric titration with 0.01 mol/L $AgNO_3$ under acidic conditions with nitric acid. The measured halide ion concentration was converted to the content of NaCl in the sample in terms of weight %. If the halide salt content in the sample is too high, the weight of sample is decreased such that the endpoint is reached with 1-5 ml of 0.01 mol/L $AgNO_3$.

(3) Electroconductivity of Leaching Water 5.0 g of the sample was weighed in a 100 ml polypropylene container and dissolved in 30 ml of dioxane completely. To the solution was added 50 ml of deionized water portionwise with stirring to precipitate a portion of brominated phenoxytriazine dissolved in dioxane. The electroconductivity of the resulting aqueous slurry was measured at 24.5-25.5° C. using an electroconductivity meter CM-30S and an electrode CGT-511B (cell constant=0.966/cm) both available from Toa Dempa Kogyo Co. Ltd. All containers, instruments and liquids (dioxane, water) were used after verifying to have an electroconductivity of less than 1×10⁻⁶ S/cm in the blank test.

Example 1

To a 500 ml flask equipped with a stirrer, a thermometer and a reflux condenser were charged with 370 ml of methylcellosolve, 7.2 g (0.18 mol) of flaky sodium hydroxide, 59.15 g (0.18 mol) of tribromophenol, and 0.10 g of calcium carbonate (9% of cyanuric chloride). The mixture was heated to 60° C. and 11.1 g (0.06 mol) of cyanuric chloride was added portionwise to the mixture over 3 minutes with stirring whereupon the inner temperature elevated to 70° C. As the reaction proceeds, the mixture became a slurry. Then the mixture was heated to 110° C. and the reaction was continued at this temperature to completion. The reaction mixture was allowed to cool to room temperature and filtered on a Buchner funnel. The filter cake was washed first with 100 ml of methanol and then with 100 ml of water each at several times until the NaCl content in the washing reached below 100 ppm. Three times washing with water was needed until the NaCl content of the washing decreased below the above level. The wet filter cake was dried in an over at 130° C. until an equilibrium was reached to give 56.3 g (88%) of the desired product. The product showed to have a NaCl content of 350 ppm and an electroconductivity of leaching water of 40×10⁻⁶ S/cm.

Example 2

To the same flask as used in Example 1 were charged with 100 ml of acetone, 99.2 g (0.3 mol) of tribromophenol, 50 g of 25% aqueous solution of sodium hydroxide (0.31 mol as NaOH), and 0.2 g of titanium dioxide (1.1% of cyanuric chloride). The mixture was heated to reflux. Then a solution of 18.4 g (0.1 mol) of cyanuric chloride in 100 ml of acetone was added dropwise to the mixture over 30 minutes, and the reaction mixture in the form of slurry was allowed to react at reflux temperature for additional 3 hours. After cooling to room temperature, the reaction mixture was filtered and the filter cake was washed first with 100 ml of acetone and then with 100 ml of water each at several times until the NaCl content in the washing decreased below 100 ppm. Three times washing with water was needed until the above NaCl level was reached. The wet filter cake was dried in an oven at 130° C. until an equilibrium was reached to give 102 g (96%) of the desired product. The product showed to have a NaCl content of 140 ppm and an electroconductivity of leaching water of 18×10⁻⁶ S/cm.

Example 3

To the same flask as used in Example 1 were charged with 150 g of water, 17.1 g (0.43 mol) of flaky sodium hydroxide, 0.07 g of sodium sulfite, and 12.5 mg (0.05% of cyanuric chloride) of fumed silica. The mixture was stirred to obtain a homogeneous solution and then cooled to 10° C. To this was added 136 g (0.136 mol) of tribromophenol. Separately, 25.0 g (0.136 mol) of cyanuric chloride was dissolved in 160 g of methylene chloride and 1.0 g of 30% aqueous solution of trimethylamine was added thereto. The cyanuric chloride solution thus prepared was added dropwise to the tribromophenol solution in the flask at a temperature of 3-30° C. After the addition the reaction mixture was heated to reflux temperature for 30 minutes to complete the reaction. Then methylene chloride was distilled off under atmospheric pressure. The residue was allowed to cool to room temperature and the resulting precipitate was filtered off and washed with 100 ml of water each at several times until the NaCl content in the washing decreased below 100 ppm. Three times washing was needed until the above NaCl level was reached. The washed filter cake was dried in an oven at 130° C. until an equilibrium was reached to give 284.3 g (98%) of the desired product. The product showed to have a NaCl content of 220 ppm and an electroconductivity of leaching water of $20 \times 10^{-6}$ S/cm.

Example 4

To the same flask as used in Example 1 were charged with 96 g of water, 34.2 g (0.86 mol) of flaky sodium hydroxide and 0.14 g of sodium sulfite while stirring. The resulting solution was cooled to 10° C. To the solution were added 130 g of methylene chloride and 272 g (0.82 mol) of tribromophenol. Then 50.0 g (0.27 mol) of cyanuric chloride and 75 mg of fumed silica (0.3% of cyanuric chloride) were gradually added to the solution at a temperature of 3-30° C. After the addition, the reaction mixture was heated to reflux temperature for additional 30 minutes to complete the reaction, and then methylene chloride was distilled off under atmospheric pressure. The residue was allowed to cool to room temperature and the resulting precipitate was filtered off. The filter cake was repeatedly washed with 100 ml of water each time until the NaCl content in the washing reached below 100 ppm. Three times washing was needed to decrease the NaCl level below 100 ppm. The washed filter cake was dried in an oven at 130° C. until an equilibrium was reached to give 284.3 g (98%) of the desired product. The product showed to have a NaCl content of 90 ppm and an electroconductivity of leaching water of $15 \times 10^{-6}$ S/cm.

Example 5

The procedure of Example 3 was repeated except that 50 mg of precipitated barium sulfate (0.2% of cyanuric chloride) was added to the reaction system in place of 12.5 mg of fumed silica. Three times washing with water was needed to decrease the NaCl concentration in the washing below 100 ppm. The washed filter cake was dried in an oven at 130° C. until an equilibrium was reached to give 142.2 g (98%) of the desired product. The product showed to have a NaCl content of 110 ppm and an electroconductivity of leaching water of $20 \times 10^{-6}$ S/cm.

Example 6

The procedure of Example 3 was repeated except that 0.25 g of talc (1.0% of cyanuric chloride) was added to the reaction system in place of 12.5 mg of fumed silica. Three times washing with water was needed to decrease the NaCl concentration in the washing below 100 ppm. The washed filter cake was dried in an oven at 130° C. until an equilibrium was reached to give 142.3 g (98%) of the desired product. The product showed to have a NaCl content of 70 ppm and an electroconductivity of leaching water of $12 \times 10^{-6}$ S/cm.

Example 7

The procedure of Example 4 was repeated except that 0.5 g of aluminum polyphosphate was added to the reaction system in place of 75 mg of fumed silica. Three times washing with water was needed to decrease the NaCl concentration in the washing below 100 ppm. The washed filter cake was dried in an oven at 130° C. until an equilibrium was reached to give 285.0 g (98%) of the desired product. The product showed to have a NaCl content of 180 ppm and an electroconductivity of leaching water of $22 \times 10^{-6}$ S/cm.

Example 8

The procedure of Example 4 was repeated except that 0.5 g of zirconium dioxide (1.0% of cyanuric chloride) was added to the reaction system in place of 75 mg of fumed silica. Three times washing with water was needed to decrease the NaCl concentration in the washing below 100 ppm. The washed filter cake was dried in an oven at 130° C. until an equilibrium was reached to give 283.5 g (98%) of the desired product. The product showed to have a NaCl content of 100 ppm and an electroconductivity of leaching water of $17 \times 10^{-6}$ S/cm.

Example 9

To the same flask as used in Example 1 were charged with 150 g of water, 17.1 g (0.43 mol) of flaky sodium hydroxide, 0.07 g of sodium sulfite, and 0.4 g of calcium chloride. Then 4.0 g of 10% phosphoric acid was gradually added to the mixture with stirring whereupon a milky solution in which fine particles of water-insoluble calcium phosphate are suspending was obtained. The mean particle diameter of calcium phosphate was measured as about 3 microns and the total weight of the suspended calcium phosphate particles was calculated as about 0.5 g (about 2% of cyanuric chloride) from the amounts of starting reactants. The milky solution was cooled to 10° C. and 136 g (0.136 mol) of tribromophenol was dissolved in this solution. Using the resulting tribromophenol solution, the reaction with cyanuric chloride was carried out as in Example 3. Three times washing with water was needed to decrease the NaCl concentration in the washing below 100 ppm. The washed filter cake was dried in an oven at 130° C. until an equilibrium was reached to give 142 g (98%) of the desired product. The product showed to have a NaCl content of 230 ppm and an electroconductivity of leaching water of $36 \times 10^{-6}$ S/cm.

Example 10

To the same flask as used in Example 1 were charged with 150 g of water, 17.1 g (0.43 mol) of flaky sodium hydroxide, 0.07 g of sodium sulfite, and 0.75 g (3.0% of cyanuric chloride) of antimony trioxide. The mixture was stirred to obtain a homogeneous solution and then cooled to 10° C. To this was added 136 g (0.136 mol) of tribromophenol. Separately, 25.0 g (0.136 mol) of cyanuric chloride was dissolved in 160 g of methylene chloride and 1.0 g of 30% aqueous solution of trimethylamine was added thereto. The cyanuric chloride solution thus prepared was added dropwise to the tribromophenol solution in the flask at a temperature of 3-30° C. After the addition the reaction mixture was heated to reflux temperature for 30 minutes to complete the reaction. Then methylene chloride was distilled off under atmospheric pressure. The residue was allowed to cool to room temperature and the resulting precipitate was filtered off and washed with 100 ml of water each at several times until the NaCl content in the washing decreased below 100 ppm. Three times washing was needed until the above NaCl level was reached. The washed filter cake was dried in an oven at 130° C. until an equilibrium was reached to give 285.0 g (98%) of the desired product. The product showed to have a NaCl content of 84 ppm and an electroconductivity of leaching water of $16\times10^{-6}$ S/cm.

Comparative Example 1

Example 1 was repeated in the absence of calcium carbonate. The product showed to have a NaCl content of 2,300 ppm and an electroconductivity of leaching water of $180\times10^{-6}$ S/cm.

Comparative Example 2

Example 2 was repeated in the absence of titanium dioxide. The product showed to have a NaCl content of 4,600 ppm and an electroconductivity of leaching water of above $200\times10^{-6}$ S/cm.

Comparative Example 3

Example 3 was repeated in the absence of fumed silica. The product showed to have a NaCl content of 7,300 ppm and an electroconductivity of leaching water of above $200\times10^{-6}$ S/cm.

Comparative Example 4

Example 4 was repeated in the absence of fumed silica. The product showed to have a NaCl content of 11,500 ppm and an electroconductivity of leaching water of above $200\times10^{-6}$ S/cm.

Comparative Example 5

To the same flask as used in Example 1 were charged with 100 g of the product of Comparative Example 4 having a mean diameter of 100 microns and 300 ml of methanol. The mixture was stirred at reflux temperature for 1 hour and then allowed to cool to room temperature. Solids were recovered from the mixture by filtration, washed with 2×100 ml of water, and dried in an oven at 130° C. until an equilibrium was reached. The NaCl content of the product decreased to 8,900 ppm by the above treatment but the electroconductivity of leaching water remained above $200\times10^{-6}$ S/cm.

Comparative Example 6

The procedure of Comparative Example 5 was repeated after pulverizing the product of Comparative Example 4 from 100 microns mean diameter to 5 microns mean diameter. The NaCl content decreased to 970 ppm while the electroconductivity of leaching water decreased to $85\times10^{-6}$ S/cm by the above treatment.

Part II. Evaluation of Brominated Phenoxytriazine

Materials
1) Brominated Phenoxytriazine;
  Products of Examples 1-4 and Comparative Examples 1-6 were used.
2) Fiber Glass Reinforced Polybutylene Terephthalate;
  Novaduran 5010G30 available from Mitsubishi Engineering Plastics.
3) Antimony Trioxide;
  Pyroguard AN-800(T) available from Dai-Ichi Kogyo Seiyaku Co., Ltd.
4) Antioxidant;
  Irganox 245 available Ciba Specialty Chemicals.

Preparation of Test Pieces

| Material | Parts |
|---|---|
| Fiber glass reinforced polybutylene terephthalate | 100.0 |
| Brominated phenoxytriazine | 12.0 |
| Antimony trioxide | 4.0 |
| Antioxidant | 0.2 |

The mixture of the above formulation was kneaded in a twin screw extruder having an inner diameter of 20 mm at 250° C. and extruded through a die. The extrudate was cooled and cut into pellets. After drying at 80° C. under reduced pressure the pellets were injection molded into various test pieces for respective testing. The mold temperature was 60° C. The test pieces were stored in a desiccator until immediately before use.

Test Method
(1) Melt Mass Flow Rate (MFR)
  Using the pellets before molding, MFR was determined according to JIS K7210, method A at a temperature of 250° C. and a load of 2.116 kg.
(2) Flame Retardancy
  The flame retardancy was evaluated by the vertical combustion method according to UL-94 standard. The size of test piece was 127 mm in length, 12.5 mm in width and 0.8 mm in thickness.
(3) Heat Distortion Temperature (HDT)
  HDT was determined according to JIS K6810. The size of test piece was 127 mm in length, 12.7 mm in height and 3.2 mm in width. The heat distortion temperature refers to a temperature at which the test piece is distorted through 0.254 mm under a load of 4.6 $kgf/cm^2$.
(4) Flexural Strength
  The flexural strength was determined according to JIS K7203 using the same test piece used for determining HTD. The test was carried out at a distance between supporting point of 68 mm and a bending rate of 2 mm/min. The flexural strength was calculated from the maximum bending load.
(5) Tracking Resistance
  The tracking resistance was determined according to JIS C2134. The test piece was a square plate of 50×50×3.2 mm size having smooth surfaces.
(6) Tracking Resistance after Accelerated Aging
  The same test piece as used in the method (5) was subjected 10 cycles of placing the test piece first at a temperature of 80° C. and at a relative humidity of 90% for 24 hours and then at a temperature of 25° C. and at a relative humidity of 20% for 24 hours. After the treatment, the test piece was dried at 80° C. under reduce pressure for 24 hours and allowed to cool to room temperature in a desiccator. During the above treatment, care was taken to leave the test surfaces untouched. After the above treatment, the tracking resistance was determined as above.
(7) Heat Stability
  The same test piece as used in the method (5) was used in this test. The test piece was hot pressed at 280° C. for 30 minutes. Color difference deltaE of the heat treated test piece was determined by measuring the color before and after the heat treatment. The heat stability was evaluated by the color difference deltaE according to the following schedule.
  Good: deltaE<5
  Fair: deltaE=5-10
  Not Good: deltaE>10

(8) Metal Mold Corrosiveness 2 g of the resin pellets for preparing the test pieces was placed on a clean surface of quenched SKD-11 steel plate and covered with inverted Petri dish. The steel plate with the resin pellets thereon was heated in an oven at 280° C. for 1 hour and then removed from the oven. The surface of the steel plate in the area covered by the Petri dish was visually inspected if rust or other indications of corrosion developed.

Results

The results of Part I and Part II are shown in tables 1-2 and Table 3 respectively.

the electroconductivity of water used for leaching the reaction product, the parameter representing the content of water soluble ionizable impurities, was reduced below $50 \times 10^{-6}$ S/cm. The products of Examples 1-10 contain a detectable level of a metal species corresponding to the water-insoluble metal compound added to the reaction system. The detection of a metal specie, in this case, demonstrates that the contents of NaCl and other ionizable impurities in the crystalline product have been reduced to an acceptable level.

The products of Comparative Examples 1-4 showed to contain a large amount of NaCl produced as by-product.

TABLE 1

| Item | EXAMPLE | | | | | | | | | |
|---|---|---|---|---|---|---|---|---|---|---|
| | 1 | 2 | 3 | 4 | 5 | 6 | 7 | 8 | 9 | 10 |
| Insoluble metal compound | $CaCO_3$ | $TiO_2$ | $SiO_2$ | $SiO_2$ | $BaSO_4$ | Talc | P3—Al[1] | $ZrO_2$ | Ca—$PO_4$[2] | $Sb_2O_3$ |
| Amount (% of cyanuric chloride) | 9.0 | 1.1 | 0.05 | 0.3 | 0.2 | 1.0 | 1.0 | 1.0 | about 2.0 | 3.0 |
| Yield (%) | 88 | 96 | 97 | 98 | 98 | 98 | 98 | 98 | 98 | 98 |
| NaCl content (ppm) | 350 | 140 | 220 | 90 | 110 | 70 | 180 | 100 | 230 | 84 |
| Metal Species | Ca | Ti | Si | Si | Ba | Mg | Al | Zr | Ca | Sb |
| Metal content (ppm) | 260 | 100 | 8 | 57 | 27 | 74 | 106 | 30 | 15 | 315 |
| Conductivity of leaching water ($\times 10^{-6}$ S/cm) | 40 | 18 | 20 | 15 | 20 | 12 | 22 | 17 | 36 | 16 |

[1] Aluminum polyphosphate;
[2] Reaction product between $CaCl_2$ and $H_3PO_4$

TABLE 2

| Item | COMPARATIVE EXAMPLE | | | | | |
|---|---|---|---|---|---|---|
| | 1 | 2 | 3 | 4 | 5 | 6 |
| Insoluble metal compound | Not present | Not present | Not present | Not present | Not present | Not present |
| Yield (%) | 86 | 95 | 97 | 98 | — | — |
| NaCl content (ppm) | 2,300 | 4,600 | 7,300 | 11,500 | 8,900 | 970 |
| Conductivity of leaching water ($\times 10^{-6}$ S/cm) | 180 | >200 | >200 | >200 | >200 | 85 |

TABLE 3

| Item | Run No. | | | | | | |
|---|---|---|---|---|---|---|---|
| | 1 | 2 | 3 | 4 | 5 | 6 | 7 |
| Brominated phenoxytriazine | Ex. 1 | Ex. 2 | Ex. 3 | Ex. 4 | Comp. Ex. 4 | Comp. Ex. 5 | Comp. Ex. 6 |
| MFR, g/10 min. | 22 | 22 | 22 | 22 | 22 | 22 | 22 |
| Flame retardancy (VL-94) | V-0 | V-0 | V-0 | V-0 | V-0 | V-0 | V-0 |
| HDT, ° C. | 200.5 | 200.5 | 200.5 | 200.5 | 200.5 | 200.5 | 200.5 |
| Flexural strength, MPa | 212 | 210 | 214 | 214 | 208 | 210 | 212 |
| Tracking resistance, V | 420 | 430 | 430 | 430 | 340 | 360 | 380 |
| Tracking resistance after aging, V | 410 | 430 | 430 | 430 | 210 | 260 | 300 |
| Decrease in tracking resistance, V | 10 | 0 | 0 | 0 | 130 | 100 | 80 |
| Heat resistance | Good | Good | Good | Good | Not good | Not good | Not good |
| Corrosiveness | No | No | No | No | Yes | Yes | Yes |

As demonstrated by Examples 1-10, it is possible to drastically reduce the content of NaCl in the reaction product by adding an amount of a water-insoluble polyvalent metal compound to the reaction system. At the same time, Attempts have been made in Comparative Example 5 to reduce the NaCl content by leaching the product with methanol in which NaCl is soluble. However, the reduction of NaCl content was only up to about 20%. In order to improve the leaching efficiency, the reaction product was pulverized before leaching in Comparative Example 6. The content of NaCl was decreased to about one tenth. From the results of Comparative Examples 1-6, it is considered that several additional steps such as leaching and pulverizing steps are essential to reduce the NaCl content from the products of prior art processes. These additional steps are disadvantageous not only in terms of productivity but also economically.

The products of Examples and Comparative Examples show distinctive difference in performance when used for producing flame retarded plastic articles. The hue and mechanical strength properties are comparable between them but improvements may be seen in the products of Examples in the durability of electroproperties, particularly after experiencing high/low temperature and humidity hysteresis. The product of Examples have been proven to have no corrosiveness against metallic molds.

The invention claimed is:

1. A flame retardant composition for flammable plastic materials consisting essentially of
particulate 2,4,6-tris(2,4,6-tribromophenoxy)-1,3,5-triazine containing 1 to 1000 ppm of a metal species of a water-insoluble polyvalent metal compound having a solubility in water of less than 1 g/L at 25° C.,
wherein said water-insoluble polyvalent metal compound is antimony trioxide, and said water-insoluble polyvalent metal compound is being present in said particulate 2,4,6-tris(2,4,6-tribromophenoxy)-1,3,5-triazine in a physically indiscrete form, wherein said composition is prepared by reacting an alkali metal salt of 2,4,6-tribromophenol and cyanuric chloride in the presence of 0.01 to 10% by weight of finely divided particles of a water-insoluble polyvalent metal compound, based on the weight of cyanuric chloride, and wherein said composition contains at least one halide ion source and the content of halide ion sources calculated as NaCl in said composition is less than 500 ppm when determined by the potentiometric titration with $AgNO_3$.

2. The flame retardant composition according to claim 1, wherein the amount of said metal species is up to 500 ppm.

3. The flame retardant composition according to claim 1, wherein electroconductivity of leaching water of the composition is less than $50 \times 10^{-6}$ S/cm.

4. The flame retardant composition according to claim 1, wherein the content of halide ion sources calculated as NaCl of the composition is less than 250 ppm when determined by the potentiometric titration with $AgNO_3$.

5. The flame retardant composition according to claim 1, wherein said water-insoluble polyvalent metal compound has a mean particle diameter of less than 10 microns.

6. The flame retardant composition according to claim 1, wherein said finely divided particles of the water-insoluble polyvalent metal compound is present in a solution of said alkali metal salt of tribromophenol, and wherein said cyanuric chloride reactant is added to said solution.

7. The flame retardant composition according to claim 1, wherein said finely divided particles of the water-insoluble polyvalent metal compound and said cyanuric chloride reactant are simultaneously added to a solution of said alkali metal salt of tribromophenol.

8. The flame retardant composition according to claim 1, further comprising the steps of filtering the reaction mixture to recover the precipitated reaction product, and washing the recovered reaction product with water and/or an organic solvent in which an alkali metal halide is soluble.

9. The flame retardant composition according to claim 8, further including the step of drying said reaction product after washing.

10. The flame retardant composition according to claim 1, wherein the content of halide ion sources calculated as NaCl in said composition is from 70 ppm to less than 500 ppm when determined by the potentiometric titration with $AgNO_3$.

11. A process for producing a flame retardant composition for flammable plastic materials comprising 2,4,6-tris(2,4,6-tribromophenoxy)-1,3,5-triazine according to claim 1, said process consisting essentially of reacting an alkali metal salt of 2,4,6-tribromophenol and cyanuric chloride in the presence of 0.01 to 10% by weight of finely divided particles of a water-insoluble polyvalent metal compound, based on the weight of cyanuric chloride.

12. A process according to claim 11, wherein said water-insoluble polyvalent metal compound has a mean particle diameter of less than 10 microns.

13. A process according to claim 11, wherein said finely divided particles of the water-insoluble polyvalent metal compound is present in a solution of said alkali metal salt of tribromophenol, and wherein said cyanuric chloride reactant is added to said solution.

14. A process according to claim 11, wherein said finely divided particles of the water-insoluble polyvalent metal compound and said cyanuric chloride reactant are simultaneously added to a solution of said alkali metal salt of tribromophenol.

15. A process according to claim 11, further comprising the steps of filtering the reaction mixture to recover the precipitated reaction product, and washing the recovered reaction product with water and/or an organic solvent in which an alkali metal halide is soluble.

16. A process according to claim 15, further including the step of drying said reaction product after washing.

* * * * *